US008858919B2

(12) United States Patent
Andersen

(10) Patent No.: US 8,858,919 B2
(45) Date of Patent: *Oct. 14, 2014

(54) METHOD OF PROVIDING FAST RELIEF TO A USER OF A NICOTINE CHEWING GUM

(71) Applicant: Carsten Andersen, Vejle (DK)

(72) Inventor: Carsten Andersen, Vejle (DK)

(73) Assignee: Fertin Pharma A/S (DK)

( * ) Notice: Subject to any disclaimer, the term of this patent is extended or adjusted under 35 U.S.C. 154(b) by 0 days.

This patent is subject to a terminal disclaimer.

(21) Appl. No.: 13/963,480

(22) Filed: Aug. 9, 2013

(65) Prior Publication Data

US 2013/0323184 A1 Dec. 5, 2013

Related U.S. Application Data

(63) Continuation of application No. 11/791,945, filed as application No. PCT/DK2004/000833 on Nov. 30, 2004, now Pat. No. 8,524,196.

(51) Int. Cl.
*A61K 9/58* (2006.01)
*A61K 31/465* (2006.01)
*A61K 9/68* (2006.01)

(52) U.S. Cl.
CPC ............. *A61K 31/465* (2013.01); *A61K 9/0058* (2013.01)
USPC .......................... 424/48; 424/78.15; 514/243

(58) Field of Classification Search
None
See application file for complete search history.

(56) References Cited

U.S. PATENT DOCUMENTS

| | | | |
|---|---|---|---|
| 3,845,217 A | 10/1974 | Ferno et al. | |
| 3,877,468 A | 4/1975 | Lichtneckert et al. | |
| 3,901,248 A | 8/1975 | Lichtneckert et al. | |
| 5,488,962 A | 2/1996 | Perfetti | |
| 6,627,234 B1 | 9/2003 | Johnson et al. | |
| 2002/0039560 A1 | 4/2002 | Ream et al. | |
| 2002/0098264 A1* | 7/2002 | Cherukuri et al. | 426/3 |
| 2002/0102304 A1 | 8/2002 | Pinney et al. | |
| 2003/0099740 A1 | 5/2003 | Colle et al. | |
| 2004/0028772 A1* | 2/2004 | Andersen | 426/3 |
| 2004/0115305 A1 | 6/2004 | Andersen et al. | |

FOREIGN PATENT DOCUMENTS

| | | |
|---|---|---|
| CN | 1075851 A | 9/1993 |
| EP | 0150934 A2 | 8/1985 |
| JP | S60186250 A | 9/1985 |
| JP | 2003509455 A | 3/2003 |
| JP | 2003530865 A | 10/2003 |
| JP | 2005531317 A | 10/2005 |
| JP | 2005531319 A | 10/2005 |
| JP | 2006506422 A | 2/2006 |
| WO | 9317571 A1 | 9/1993 |
| WO | 0013662 A2 | 3/2000 |
| WO | 0025598 A1 | 5/2000 |
| WO | 0056281 A1 | 9/2000 |
| WO | 02076229 A1 | 10/2002 |
| WO | 02102357 A1 | 12/2002 |
| WO | 2004004479 A1 | 1/2004 |
| WO | 2004004480 A1 | 1/2004 |
| WO | 2004043388 A2 | 5/2004 |
| WO | 2004056363 A2 | 7/2004 |
| WO | 2006000232 A1 | 1/2006 |

OTHER PUBLICATIONS

XP—002338413, "2.9.25 Chewing Gum, Medicated, Drug Release From"; European Pharmacopoeia, 4th Edition, 2002; 2 pages.
Kvist, et al.; "Apparatus for Studying in Vitro Drug Release from Medicated Chewing Gums"; International Journal of Pharmaceutics, vol. 189, 1999, pp. 57-65.
Hunter, et al.; "Calcium Channel Blockers 1: A Review of Their Mechanisms of Action"; Pharmacy International, Nov. 1985, pp. 267-271.
Djordjevic, et al. "Doses of Nicotine and Lung Carcinogens Delivered to Cigarette Smokers"; Journal of the National Cancer Institute, 2000, 92(2), pp. 106-111.
Kvist, et al.; "Equipment for Drug Release Testing of Medicated Chewing Gums"; Journal of Pharmaceutical and Biomedical Analysis; vol. 22, No. 3, Apr. 2000; pp. 405-411.
Food and Drug Administration, CFR, Title 21, Section 172.615, as "Masticatory Substances of Natural Vegetable Origin" Printed 2006, 2 pages.
International Search Report and Written Opinion of the International Searching Authority Application No. PCT/DK2004/000833 Completed: Jul. 29, 2005; Mailing Date: Aug. 16, 2005 14 pages.
Martindale, The Extra Pharmacopoeia 28th Ed., Reynolds, James E. F., Editor, the Pharmaceutical Press, London (1982).
Author: Unknown; "Mastic (Plant Resin)"; From Wikipedia, the free encyclopedia; web page http://en.wikipedia.org/wiki/Mastic_(plant_resin) . . . web page last modified on May 25, 2011; 4 pages.
Le Houezec, J.; "Role of Nicotine Pharmokinetics in Nicotine Addiction and Nicotine Replacement Therapy: A Review"; Intl. J. Tuberc. Lung Dis., 2003, 7(9), pp. 811-819.
Manly, et al.; "Substances Capable of Decreasing the Acid Solubility of Tooth Enamel"; J. Dent. Res.; vol. 28, No. 2; (1949) pp. 160-171.
Balfour, D.; "The Neurobiology of Tabacco Dependence: A Commentary, Respiration"; 2002, 69, pp. 7-11.
US Code Federal Regulations, Title 21, vol. 3, Sec. 182.5013-182. 8997 (Apr. 1, 2005).; 3 pages.

(Continued)

*Primary Examiner* — Frederick Krass
*Assistant Examiner* — Michael P Cohen
(74) *Attorney, Agent, or Firm* — St. Onge Steward Johnston & Reens LLC

(57) ABSTRACT

The invention relates to a method of relieving nicotine craving comprising the steps of providing at least one chewing gum comprising tobacco alkaloid to a user, providing relief of nicotine craving to said user by transferring of tobacco alkaloid from the chewing gum to the human body of said user by chewing of said chewing gum, said chewing of said chewing gum comprising a chewing process involving a transfer of tobacco alkaloid from said chewing gum above a threshold transfer rate in the period of about ½ minute to about 2½ minutes from initiation of said chewing process.

38 Claims, 4 Drawing Sheets

(56) References Cited

OTHER PUBLICATIONS

State Intellectual Property Office of People's Republic of China The First Office Action Application No. 201210328340.8 Issued: Jun. 2, 2013 3 pages.

Patent Office of the People's Republic of China Search Report Application No. 201210328340.8 Date: Jun. 13, 2013 2 pages.

Japanese Patent Office Notification of Reasons for Rejection Application No. 2010-274632 Mailing Date: Mar. 21, 2013 4 pages.

* cited by examiner

METHOD OF PROVIDING FAST RELIEF TO A USER OF A NICOTINE CHEWING GUM

BACKGROUND OF THE INVENTION

Craving or Addiction

Medical and scientific communities in the US agree that nicotine is addictive. Nicotine meets both the psychological and physiological measures of addiction:

Psychological—people who are addicted to something will use it compulsively, without regard for its negative effects on their health or life. A good example would be someone who continues to smoke, even as they use an oxygen tank to breathe because of the damage smoking has done to their lungs.

Physiological—neuroscientists call anything that turns on the reward pathway in the brain addictive. Because stimulating this neural circuitry makes you so good, you will continue to do it again and again to get those feelings back.

When smokers abruptly stop smoking—the body cannot function the same way in the absence of the drug as it did before, the physiological effects for nicotine remain, at least in the short term. They will experience: Irritability, anxiety, depression and craving for nicotine.

Over a period these symptoms and physiological changes subside. It is in this period alternative methods of nicotine delivery is essential in order to succeed quitting smoking.

Nicotine:

Nicotine normally makes up about 5% of a tobacco plant, by weight. Cigarettes contain 8-20 mg of nicotine depending on the brand, but only approximately 1 mg is actually absorbed by your body when you smoke a cigarette.

Nicotine's effects are short-lived, lasting only 40 minutes to a couple of hours. This leads people to smoke tobacco periodically throughout the day to dose themselves with nicotine. Within 10-15 seconds of inhaling, most smokers are in the throes of nicotine's effects.

Different approaches may be made in order to counteract craving related to absence of nicotine in the blood.

Many pharmacotherapies have been developed or explored for aiding smokers to cease smoking. The predominant one is nicotine replacement therapies. Nicotine replacement therapies involve the administration of nicotine through suitable delivery systems. Nicotine replacement products available on the market include nicotine transdermal patches, inhalators, nicotine nasal spray or nicotine chewing gum. These types of products, like cigarettes, deliver nicotine to the blood via diffusion of nicotine through the skin or the mucous membrane.

Nicotine transdermal patches release nicotine into the bloodstream through the skin. A patch is applied each day to a different area of dry, clean, non-hairy skin and left as long as recommended on the product labelling—typically the non-sleeping hours of a day. Using the product generates a constant low concentration of nicotine to the blood over the period applied.

Nicotine nasal spray is inhaled into the person's nose from a pump bottle and absorbed through the nasal lining into the bloodstream. This form of nicotine delivery system generates a fast increase of nicotine concentration in the blood—almost as fast as the cigarette.

Nicotine inhalator enters the user's mouth through a mouthpiece attached to a plastic cartridge. Although the product is called an "inhaler", it does not deliver nicotine to the lungs the way a cigarette does. Almost all of the nicotine travels only as far as the mouth and throat, where it is absorbed through the mucous membrane.

Nicotine chewing gum releases nicotine into the bloodstream through the lining of the mouth, i.e. the mucous membrane. Unlike gum chewed for pleasure, nicotine gum requires a measured routine—it is chewed slowly until a slight tingling occurs or a peppery taste comes out, then it is placed between the check and gum until the taste or tingling is almost gone. The cycle is typically repeated for about 30 minutes per gum. Products available slowly build up the nicotine blood concentration over the first 10-15 minutes of chewing.

The present invention relates to counteracting of craving by means of nicotine holding chewing gum.

Counteracting of craving by means of nicotine holding chewing gum as such is well-known within the art.

Basically two different paths have been followed in the prior art, alone or in combination.

The original approach was to incorporate nicotine in chewing gum and then match the release of chewing gum with the overall total desired release of nicotine over the entire chewing period. Typically, such an approach involves considerations with respect to the release of nicotine over a day compared to one or several different smoking patterns.

A further attempt to improve the counteracting of craving by means of chewing gum is to incorporate nicotine in e.g. the coat of a coated chewing gum. Such an approach may be referred to as biphasic within the art, i.e. the approach of providing an initial significant dose of nicotine immediately after chewing of a chewing gum has been initiated and then subsequently, providing a second long term dose subsequently. Such subsequent dose is also referred to as maintenance dose may e.g. last from about 10 minutes to 30 minutes of the chewing process.

A problem related to the prior art is however that some users of the chewing gum may dislike especially the initial dose and that the subsequent dose typically mismatches the expectations of the user with respect to relieving of nicotine related craving.

It is the object of the invention to obtain a chewing gum, which may be applied for an effective and user-acceptable counteracting of craving not only after use but also during use.

SUMMARY OF THE INVENTION

The invention relates to a method of relieving nicotine craving comprising the steps of providing at least one chewing gum comprising tobacco alkaloid to a user, providing relief of nicotine craving to said user by transferring of tobacco alkaloid from the chewing gum to the human body of said user by chewing of said chewing gum, said chewing of said chewing gum comprising a chewing process involving a transfer of tobacco alkaloid from said chewing gum above a threshold transfer rate in the period of about ½ minute to about 2½ minutes from initiation of said chewing process.

According to the invention a transfer of nicotine or generally a tobacco alkaloid is maintained at a threshold transfer rate in an intermediate phase of the chewing process thereby facilitating an advantageous and effective fast relief due to the fact that transfer in this particular period affects the perception of nicotine and the resulting relief significantly e.g. compared to transfer of nicotine late in the chewing process. It is especially noted that a desired "relief kick" according to the invention involves that a typically overlooked period of the chewing process, also referred to as the intermediate phase, provide a very significant part of the desirable nicotine dose to the human body as this particular period is within the typical time allocated to the smoking of a cigarette.

According to the invention threshold transfer rate is understood as a minimum rate of nicotine transfer in a given time interval. In other words, transfer rates above this minimum rate may be applied within the scope of the invention. 2½ minutes corresponds to 150 seconds.

According to the invention it has been realised that one of the problems related to the prior art is that a relief to the user of the chewing gum is hardly obtained or at least slowly when compared to the smoking of a cigarette. It has also been realised that the provisions of the prior art related to this problem is typically concerned with the amount of released nicotine from the chewing gum and basically not giving much thought of how the actual transfer of nicotine is performed. This is both the fact with respect to conventional long term release based on a chewing time over approximately 30 minutes and the fast release of nicotine in e.g. coating. Thus, it has been realised that a very fast release of nicotine, e.g. from the coating, over the first few seconds appears to have too little influence on the first five to ten minutes of chewing due to the fact that a large part of this nicotine is swallowed and transferred to the blood merely metabolically.

According to the invention a transfer rate should be understood as a transfer rate of nicotine or tobacco alkaloid from the chewing gum to the exterior, i.e. a release rate although the basic desired performance of the chewing gum also includes a transfer from the chewing gum to the blood of the relevant human body. Such a release rate may e.g. be measured in sub-periods of 30 seconds.

In the present invention the term "tobacco alkaloid" mean nicotine or nicotine-like alkaloid such as nor-nicotine, lobeline, and the like, in the free base or pharmacologically acceptable acid addition salt form. Plant alkaloids of this type are obtainable from species of Nicotiana which is a source for nicotine and nor-nicotine, as well as species of *Lobelia* and *Lobeliaceae* (Indian tobacco) which are a source for lobeline.

Moreover, it is generally noted that specific examples and explanation specifically referring to nicotine as active agent against craving in no way restricts the scope of the invention with respect to use of other tobacco alkaloids for the same specific purpose. A specific mentioning of nicotine at any place in this application is only used for the purpose of exemplifying the invention in a tangible way and not for the purpose of excluding alternative functionally equivalents.

It should generally be noted that nicotine is a preferred tobacco alkaloid.

In the present invention, the term nicotine encompasses nicotine or a nicotine derivative in any form such as, e.g. physical forms like amorphous, crystalline, polymerphous etc. or chemical form like isomers and enantiomers etc. as well as any pharmaceutically acceptable salts, complex or solvate thereof. Nicotine may be selected from nicotine base, nicotine hydrochloride, nicotine dihydrochloride, nicotine monotartrate, nicotine bitartrate, nicotine sulfate, nicotine zinc chloride such as zinc chloride monohydrate and nicotine salicylate.

In an embodiment of the invention said tobacco alkaloid comprises nicotine.

In an embodiment of the invention said transfer rate refer to a transfer of nicotine from the chewing gum to the exterior of the chewing gum.

According to an advantageous embodiment of the invention, the chewing time may be shortened significantly for at least two different reasons, first of all: a relief is obtained by the user relatively fast due to the provisions of the invention and secondly: a mere maintenance of nicotine in the blood appears to be a dynamic more than a stationary process thereby rendering a mere continuous maintenance of nicotine less desirable to a user compared to a fast relied of initiated craving. In other words, relief of craving appears to be a dynamic process.

In an embodiment of the invention said threshold transfer rate is evaluated in sub periods of the period of about ½ minute to about 2½ minutes from initiation of said chewing process.

According to an embodiment of the invention, a sub period of 30 seconds may be advantageous for the purpose of establishing whether the transfer rate is maintained. A transfer rate measured in 30 seconds has thus proved sufficient for the purpose of obtaining a fast relief. Thus, when applying a sub period of 30 seconds, a transfer should comply with requirements defined in four sub periods, namely the sub periods ½-1 minute, 1-1½ minute, ½-2 minutes and 2-2½ minutes.

Evidently even transfer rates may be measured in shorter sub periods of time, e.g. 15 seconds may be applied. Longer sub periods may also be applied or sub periods of different length, although the period should be chosen carefully for the purpose of avoiding lowering or dropouts of the nicotine or tobacco alkaloid transfer during the intermediate release. In particular, according to the invention, a dropout should be avoided in the intermediate transfer, i.e. from about ½ to 2½ minutes as such a dropout inevitably would result in a lowered transfer in spite of the fact that a complete release of nicotine is high.

In an embodiment of the invention said chewing of said chewing gum comprising a chewing process involving a transfer of tobacco alkaloid from said chewing gum above a further threshold transfer rate in the period of about 2½ minutes to about 10 minutes from initiation of said chewing process, preferably in the period of about 2½ minutes to about 5 minutes from initiation of said chewing process.

According to a further embodiment of the invention a further threshold value may be applied for the chewing process after the initial 2½ minutes of chewing. Thus, according to an advantageous embodiment of the invention such threshold value should preferably ensure that a relatively high tobacco alkaloid transfer is obtained in the period from 2½ minutes up to 10 or preferably at least 5 minutes.

In this way, maintenance of the initially obtained relief may be obtained.

In an embodiment of the invention said threshold transfer rate results in a release of at least 2%, preferably at least 2.5% of the tobacco alkaloid comprised in said chewing gum prior to chewing, every 30 seconds in the period from minutes to about 2½ minutes from initiation of said chewing process.

According to an embodiment of the invention, the tobacco alkaloid release of the chewing is at least 2%, preferably at least 2.5%, every thirty seconds thereby maintaining a high osmotic pressure on the mucosa membrane when chewing. This initial focussing on keeping tobacco alkaloid constantly available in the mouth is in particular important in the early phase of the chewing process due to the fact that a fast relief to a user should preferably be obtained quite fast compared to conventional tobacco alkaloid containing chewing gum and that such desired fast relief requires not only just sporadic or late release phases but a maintained constantly high availability of tobacco alkaloid in the mouth over at least a part of the period usually required for smoking a cigarette.

In an embodiment of the invention said threshold transfer rate results in a release of at least 3%, preferably at least about 4% of the tobacco alkaloid comprised in said chewing gum prior to chewing, every 30 seconds in the period from about ½ minute to about 2½ minutes from initiation of said chewing process.

According to an embodiment of the invention, the tobacco alkaloid release of the chewing is at least 3%, preferably at least 4%, every thirty seconds thereby maintaining a high osmotic pressure on the mucosa membrane when chewing. This initial focussing on keeping tobacco alkaloid constantly available in the mouth is in particular important in the early phase of the chewing process due to the fact that a fast relief to a user should preferably be obtained quite fast compared to conventional tobacco alkaloid containing chewing gum and that such desired fast relief requires not only just sporadic or late release phases but a maintained constantly high availability of tobacco alkaloid in the mouth over at least a part of the period usually required for smoking a cigarette.

In an embodiment of the invention said threshold transfer rate results in a release of at least 5%, preferably at least about 6% of the tobacco alkaloid comprised in said chewing gum prior to chewing, every 30 seconds in the period from about ½ minute to about 2½ minutes from initiation of said chewing process.

According to a further advantageous embodiment of the invention a transfer rate may be established and maintained at a high level thereby featuring an improved fast relief of the user.

In an embodiment of the invention said threshold transfer rate results in a release of at least 2%, preferably at least 3% of the tobacco alkaloid comprised in said chewing gum prior to chewing, every 30 seconds in the period of about 2½ minutes to about 5 minutes from initiation of said chewing process.

According to a further advantageous embodiment of the invention, tobacco alkaloid should also be kept available at high rate in the period of about 2½ to 5 minutes after initiation of the chewing process. Again, it should be noted that such threshold rate should be complied with at virtually anytime within the interval of 2.5 to 5 minutes from initiation of the chewing process.

In an embodiment of the invention said threshold transfer rate results in a release of at least 3%, preferably at least 3.5% of the tobacco alkaloid comprised in said chewing gum prior to chewing, every 30 seconds in the period of about 2½ minutes to about 5 minutes from initiation of said chewing process.

According to a further advantageous embodiment of the invention, tobacco alkaloid should also be kept available at high rate in the period of about 2½ to 5 minutes after initiation of the chewing process. Again, it should be noted that such threshold rate should be complied with at virtually time within the interval of 2.5 to 5 minutes from initiation of the chewing process.

In an embodiment of the invention wherein said threshold transfer rate results in a release of at least 4%, preferably at least 5% of the tobacco alkaloid comprised in said chewing gum prior to chewing, every 30 seconds in the period of about 5 minutes to about 10 minutes from initiation of said chewing process.

In an embodiment of the invention said threshold transfer rate results in a release of at least 2 to 10%, preferably at least 5% of the tobacco alkaloid comprised in said chewing gum prior to chewing in the period of about 0 seconds to about 30 seconds from initiation of said chewing process.

In an embodiment of the invention said threshold transfer rate results in a release of less than 14%, preferably less than 12% of the tobacco alkaloid comprised in said chewing gum prior to chewing in the period of about 0 seconds to about 2½ minutes from initiation of said chewing process.

According to an embodiment of the invention, the initial transfer of tobacco alkaloid from the chewing gum should be kept below 12 to 14% of the tobacco alkaloid comprised in the chewing gum prior to chewing in order to avoid socalled burning or tingling. Moreover, too much releasing of e.g. nicotine would on the other hand result in that a part of the released nicotine is swallowed and therefore only effective by a metabolic transfer.

In an embodiment of the invention said threshold transfer rate results in a release of at most 18%, preferably at most 15% of the tobacco alkaloid comprised in said chewing gum prior to chewing in the period of about 10 to about 30 minutes from initiation of said chewing process.

In an embodiment of the invention said threshold transfer rate results in a release of at least 0.03 mg, preferably at least 0.04 mg of the tobacco alkaloid comprised in said chewing gum prior to chewing, every 30 seconds in the period from about 1 minute to about 2½ minutes from initiation of said chewing process.

According to the invention a build-up of nicotine or tobacco alkaloid in the blood should preferably be obtained by a maintained osmotic pressure on the mucous membrane of the mouth in the intermediate period of the chewing process, e.g. in the first ten minutes of the chewing process.

In an embodiment of the invention said threshold transfer rate results in a release of at least 0.05 mg, preferably at least 0.06 mg of the tobacco alkaloid comprised in said chewing gum prior to chewing, every 30 seconds in the period from about 1 minute to about 2½ minutes from initiation of said chewing process.

In an embodiment of the invention said threshold transfer rate results in a release of at least 0.08 mg, preferably at least 0.1 mg of the tobacco alkaloid comprised in said chewing gum prior to chewing, every 30 seconds in the period from about 1 minute to about 2½ minutes from initiation of said chewing process.

In an embodiment of the invention said threshold transfer rate results in a release of at least 0.03 mg, preferably at least 0.04 mg of the tobacco alkaloid comprised in said chewing gum prior to chewing, every 30 seconds in the period of about 2½ to about 5 minutes from initiation of said chewing process.

In an embodiment of the invention said threshold transfer rate results in a release of at least 0.05 mg, preferably at least 0.06 mg of the tobacco alkaloid comprised in said chewing gum prior to chewing, every 30 seconds in the period of about 2½ minutes to about 5 minutes from initiation of said chewing process.

In an embodiment of the invention wherein said threshold transfer rate results in a release of at least 0.08 mg, preferably at least 0.1 mg of the tobacco alkaloid comprised in said chewing gum prior to chewing, every 30 seconds in the period of about 2½ minutes to about 5 minutes from initiation of said chewing process.

In an embodiment of the invention at least 0.5 mg of tobacco alkaloid is released within the initial 10 minutes of the chewing process or preferably within the initial 5 to 8 minutes of the chewing process.

According to an embodiment of the invention even higher release should be obtained such as at least 0.8 mg of tobacco alkaloid is released within the initial 10 minutes of the chewing process or preferably within the initial 5 to 8 minutes of the chewing process.

In an embodiment of the invention wherein different parts of the chewing gum is targeted tobacco alkaloid transfer at different times or in different periods of the chewing process.

According to an embodiment of the invention different parts of the chewing gum may be targeted tobacco alkaloid transfer at different times or in different periods of the chewing process, thereby facilitating the obtaining of the desired constant transfers or at least the desired minimum transfer of the relevant period of the chewing process, i.e. typically during the first three to five minutes of the chewing process. Thus, e.g. the very initial transfer of tobacco alkaloid, i.e. the first seconds of the chewing process, may be increased by means of e.g. nicotine containing coating. Alternatively, nicotine may be comprised in beads or other release-delaying means. Again, further means may include mixture of different polymers having different release properties. Further means may include different types of buffering.

Thus the threshold transfer rate is obtained by a combination of different parts of the chewing having different release profiles.

In an embodiment of the invention wherein said chewing gum comprising a coating and wherein said coating comprises tobacco alkaloid.

According to an embodiment of the invention, tobacco alkaloid is comprised in the coating and may therefore be released quite fast in the very early stage of the chewing process.

In an embodiment of the invention said chewing gum comprises substantially hydrophilic polymers.

In an embodiment of the invention the variation of transfer rate is minimized.

According to an embodiment of the invention, the significant variations of tobacco alkaloid over time should be avoided in order to obtain an advantageous taste masking. A sudden tobacco alkaloid peak would thus be difficult to taste mask, especially when dealing with peaks occurring subsequently to the very initial chewing process. I1 and I3 as described below are examples of such smoothed release.

In an embodiment of the invention wherein said tobacco alkaloid is comprised in a ion exchange resin.

According to an embodiment tobacco alkaloid is nicotine polacrilex.

In an embodiment of the invention wherein said tobacco alkaloid comprises salts of nicotine.

In an embodiment of the invention said tobacco alkaloid comprises nicotine in its free from.

In an embodiment of the invention the tobacco alkaloid is buffered.

In an embodiment of the invention the chewing process is less than 30 minutes, preferably less than 20 minutes.

According to an embodiment the chewing process should be kept short in order to comply with the basic principles of fast relief as obtained by the desired emulation of the smoking process.

In an embodiment of the invention the chewing process is matching the smoking time of a cigarette.

In an embodiment of the invention said chewing gum comprises a polymer system in an amount of from about 2 to about 99% by weight, flavour in an amount of about 0.001 to about 30% by weight and sweeteners in an amount of about 2% to about 80% by weight.

In an embodiment of the invention said chewing gum comprises fillers in an amount of from about 0 to about 60% by weight, flavour in an amount of about 0.001 to about 30% by weight and sweeteners in an amount of about 2 to about 80% by weight.

In an embodiment of the invention said chewing gum comprises high intensity sweeteners in an amount of from about 0.001 to about 3% by weight and flavour in an amount of about 0.001 to about 30% by weight.

In an embodiment of the invention said polymer system comprises elastomers in an amount of about 0.1 to about 40% by weight of the chewing gum, preferably in an amount of about 2 to about 10% by weight of the chewing gum.

In an embodiment of the invention said polymer system comprises elastomer plasticizers in an amount of about 2 to about 60% by weight of the chewing gum, preferably in an amount of about 5 to about 30% by weight of the chewing gum.

In an embodiment of the invention said polymer system comprises wax in an amount of about 0 to about 30% by weight of the chewing gum, preferably in an amount of about 0 to about 15% by weight of the chewing gum.

In an embodiment of the invention said polymer system comprises softeners in an amount of about 2 to about 30% by weight of the chewing gum, preferably in an amount of about 5 to about 20% by weight of the chewing gum.

In an embodiment of the invention said polymer system comprises fillers in an amount of about 0 to about 50% by weight of the chewing gum, preferably in an amount of about 0 to about 30% by weight of the chewing gum.

In an embodiment of the invention said polymer system comprises antioxidants in an amount of about 0 to about 5% by weight of the chewing gum, preferably in an amount of about 0 to about 2% by weight of the chewing gum.

In an embodiment of the invention at least one piece of said chewing gum is chewed at a time.

In an embodiment of the invention at least two pieces of said chewing gum are chewed at a time.

In an embodiment of the invention at least one piece of said chewing gum is chewed a day.

In an embodiment of the invention at least one piece of said chewing gum is chewed when the person craves for nicotine.

According to an advantageous embodiment of the invention a tobacco alkaloid holding chewing may even be applied solely as a reaction on craving of a user. In other words, mere maintenance of a high nicotine level in the blood may be avoided.

In an embodiment of the invention at least one piece of said chewing is chewed when the person needs treatment including tobacco alkaloid or nicotine.

BRIEF DESCRIPTION OF THE DRAWINGS

The invention will now be described with reference to the drawings of which

DETAILED DESCRIPTION OF THE INVENTION

Figure 1:
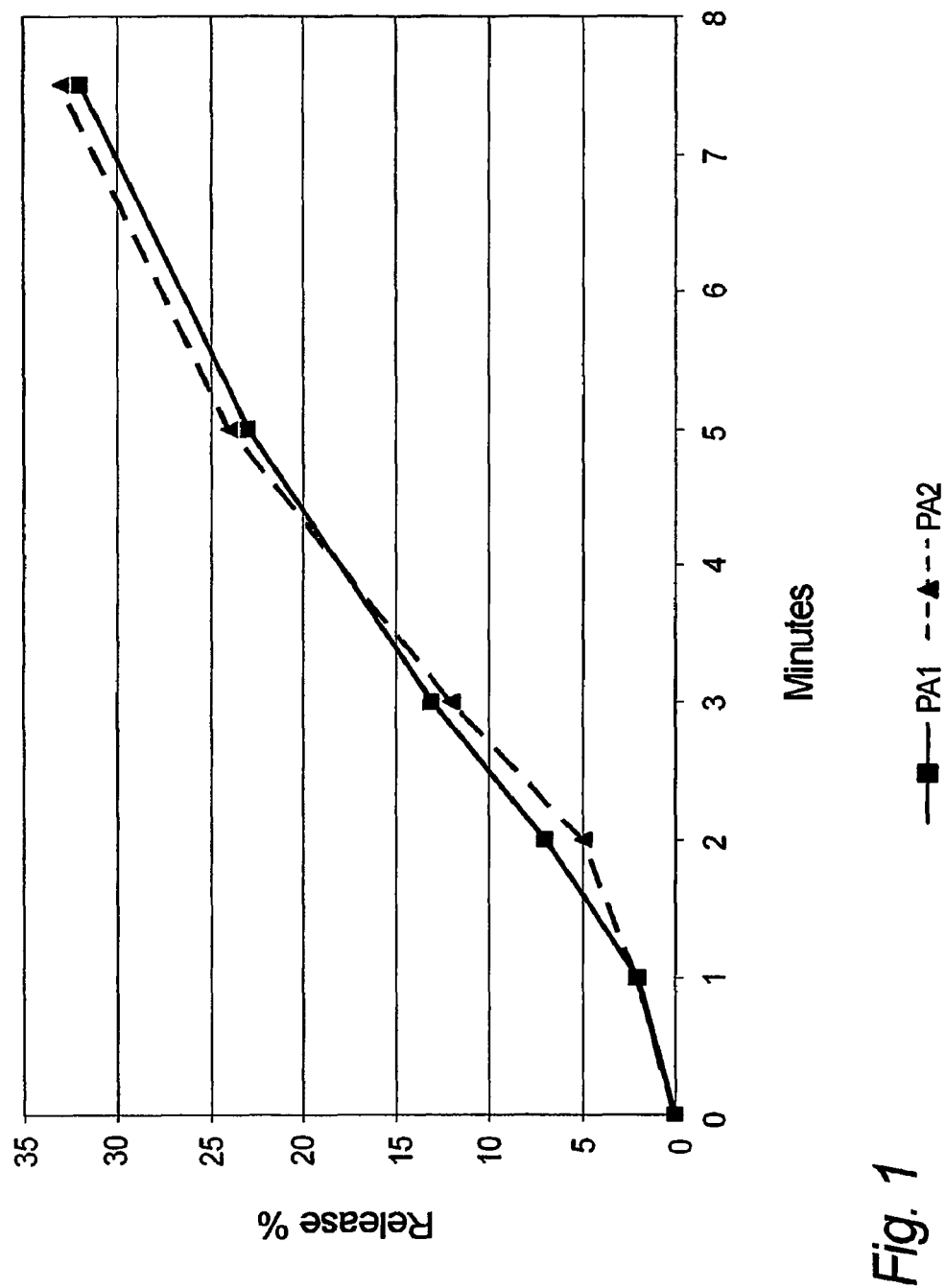
FIG. 1 shows the release profile of prior art nicotine chewing gums.

In general, a chewing gum composition typically comprises a water-soluble bulk portion, a water-insoluble chewable gum base portion and flavouring agents. The water-soluble portion dissipates with a portion of the flavouring agent over a period of time during chewing. The gum base portion is retained in the mouth throughout the chew. The term chewing gum refers to both a chewing and bubble type gum in its general sense.

The gum base is the masticatory substance of the chewing gum, which imparts the chew characteristics to the final product. The gum base typically defines the release profile of flavours and sweeteners and plays a significant role in the gum product.

The insoluble portion of the gum typically may contain any combination of elastomers, vinyl polymers, elastomer plasticizers, waxes, softeners, fillers and other optional ingredients such as colourants and antioxidants.

The composition of gum base formulations can vary substantially depending on the particular product to be prepared and on the desired masticatory and other sensory characteristics of the final product. However, typical ranges (% by weight) of the above gum base components are: 5 to 50% by weight elastomeric compounds, 5 to 55% by weight elastomer plasticizers, 0 to 40% by weight of waxes, 5 to 35% by weight softener, 0 to 50% by weight filler, and 0 to 5% by weight of miscellaneous ingredients such as antioxidants, colourants, etc.

Function of Elastomers

Elastomers provide the rubbery, cohesive nature to the gum, which varies depending on this ingredient's chemical structure and how it may be compounded with other ingredients. Elastomers suitable for use in the gum base and gum of the present invention may include natural or synthetic types.

Elastomers

The elastomer may be any water-insoluble polymer known in the art, and includes those gum polymers utilized for chewing gum and bubble gum listed in Food and Drug Administration, CFR, Title 21, Section 172,615, as "Masticatory Substances of Natural Vegetable Origin" and "Masticatory Substances, Synthetic"

Useful natural elastomers include natural rubber such as smoked or liquid latex and guayule, natural gums such as jelutong, lechi caspi, perillo, sorva, massaranduba balata, massaranduba chocolate, nispero, rosidinha, chicle, gutta percha, gutta kataiu, niger gutta, tunu, chilte, chiquibul, gutta hang kang.

Useful synthetic elastomers include high molecular weight elastomers such as butadiene-styrene copolymers, polyisobutadiene and isobutylene-isoprene copolymers, low molecular weight elastomers such as polybutene, polybutadiene and polyisobutylene, vinyl polymeric elastomers such as polyvinyl acetate, polyethylene, vinyl copolymeric elastomers such as vinyl acetate/vinyl laurate, vinyl acetate/vinyl stearate, ethylene/vinyl acetate, polyvinyl alcohol or mixtures thereof.

Butadiene-styrene type elastomers, or SBR as they may be called, typically are copolymers of from about 20:80 to 60:40 styrenes:butadiene monomers. The ratio of these monomers affects the elasticity of the SBR as evaluated by mooney viscosity. As the styrene:butadiene ratio decreases, the mooney viscosity decreases.

The structure of SBR typically consists of straight chain 1,3-butadiene copolymerized with phenylethylene (styrene) and provides the non-linear molecular nature of these elastomers. The average molecular weight of SBR is <600.000 g/mole.

Isobutylene-isoprene type elastomers, or butyl as they may be called, have molar percent levels of isoprene ranging from 0.2 to 4.0. Similar to SBR, as the isoprene:isobutylene ratio decreases, so does the elasticity, measured by mooney viscosity.

The structure of butyl rubber typically consists of branched 2-methyl-1,3-butadiene (isoprene) copolymerized with branched 2-methylpropene (isobutylene), and, as with SBR, this type of structure is non-linear in nature. The average molecular weight of SBR is in the range from 150.000 g/mole to 1.000.000 g/mole.

Polyisobutylene, or PIB as they may be called, type elastomers are polymers of 2-methylpropene and, as with SBR and butyl, are non-linear in nature. The low molecular weight elastomers provide soft chew characteristics to the gum base and still provide the elastic qualities as do the other elastomers. Average molecular weights may range from about 30,000 to 120,000 g/mole and the penetration may range from about 4 millimeters to 20 millimeters. The higher the penetration, the softer the PIB. Similar to the SBR and butyl, the high molecular weight elastomers provide elasticity the gum. Average molecular weight may range from 120.000 to 1.000.000 g/mole.

Polybutenes range in average molecular weight from about 5.000 g/mole to about 30.000 g/mole.

Function of Vinyl Polymers

Vinyl polymeric and copolymeric type elastomers provide tack resistance, vary the chew characteristics of gums made from these bases having vinyl polymers and offer hydrophilic properties beneficial to sensory perception of the final gums.

Vinyl Polymers

For vinyl copolymeric types, the amount of vinyl laurate, vinyl stearate, or ethylene present in the vinyl laurate/vinyl acetate (L/VA), vinyl stearate/vinyl acetate (VS/VA), or ethylene/vinyl acetate (EVA) copolymers respectively typically ranges from about 10 to about 60% by weight of the copolymer. Average molecular weights of these polymers may range from about 2.000 g/mole to about 100,000 g/mole.

The vinyl polymers such as polyvinyl alcohol and polyvinyl acetate have an average molecular weight from about 8.000 g/mole to about 65.000 g/mole.

Polymers of vinyl acetate (PVAc) are branched in nature. The degree of branching is increased when vinyl acetate monomers are copolymerized with vinyl laurate, vinyl stearate, ethylene and the like. The higher the degree of branching, the higher the compatibility when blended or compounded with normal-alkanic and iso-alkanic type waxes.

It is e.g. common in the industry to combine in a gum base a synthetic elastomer having a high molecular weight and a low-molecular-weight elastomer. Presently preferred combinations of synthetic elastomers include, but are not limited to, polyisobutylene and styrene-butadiene, polyisobutylene and polyisoprene, polyisobutylene and isobutylene-isoprene copolymer (butyl rubber) and a combination of polyisobutylene, styrene-butadiene copolymer and isobutylene isoprene copolymer, and all of the above individual synthetic polymers in admixture with polyvinyl acetate, vinyl acetate-vinyl laurate copolymers, respectively and mixtures thereof.

Function of Elastomer Plasticizers

Elastomer plasticizers vary the firmness of the gum base. Their specificity on elastomer inter-molecular chain breaking (plasticizing) along with their varying softening points cause varying degrees of finished gum firmness and compatibility when used in base. This may be important when one wants to provide more elastomeric chain exposure to the alkanic chains of the waxes.

Elastomer Plasticizers

Elastomer plasticizers suitable for use in the present invention include natural rosin esters often referred to as ester gums. Such elastomer plasticizers known in the art are methyl, glycerol and pentaerythritol esters of rosins and modified rosins, such as hydrogenated, dimerized and polymerized rosins. Examples are glycerol ester of wood and gum rosin, glycerol ester of partially hydrogenated wood and gum rosin, glycerol ester of polymerized wood and gum rosin, glycerol ester of partially dimerized wood and gum rosin, glycerol ester of tall oil rosin, pentaerytritol ester of wood and gum rosin, pentaerythritol esters of partially and fully hydrogenated wood and gum rosin, methyl esters of wood and gum rosins and partially and fully hydrogenated methyl esters of wood and gum rosin.

The synthetic elastomer plasticizers include terpene resins derived from alpha-pinene, beta-pinene and/or d-limonene.

The elastomer plasticizers used may be of one type or of combinations of more than one type. Typically, the ratios of one to the other are dependent on each respective softening point, the effect on flavour release, and the respective degree of tack they case to the gum. Ball and ring softening points of the rosin ester types described above may range from about 45° C. to about 120° C. Softening points of the terpene resins may range from about 60° C. to about 130° C.

Function of Waxes

Petroleum waxes aid in the curing of the finished gum made from the gum base as well as improve shelf life and texture. Wax crystal size influences the release of flavour. Those waxes high in iso-alkanes have a smaller crystal size than those waxes high in normal-alkanes, especially those with normal-alkanes of carbon numbers less than 30. The smaller crystal size allows slower release of flavour since there is more hindrance of the flavour's escape from this wax versus a wax having larger crystal sizes. The compatibility of gum bases made using normal-alkanic waxes is less when compared to gum bases made with iso-alkanic waxes.

Waxes

Petroleum wax (refined paraffin and microcrystalline wax) and paraffin wax are composed of mainly straight-chained normal-alkanes and branched iso-alkanes. The ratio of normal-alkanes to iso-alkanes varies.

The normal-alkanic waxes typically have carbon chain lengths >C-18 but the lengths are not predominantly longer than C-30. The branched and ring structures are located near the end of the chain for those waxes that are predominantly normal-alkanic. The viscosity of normal-alkanic waxes is <10 mm2/s (at 100° C.) and the combined number average molecular weight is <600 g/mole.

The iso-alkanic waxes typically have carbon lengths that are predominantly greater than C-30. The branched chains and ring structures are located randomly along the carbon chain in those waxes that are predominantly iso-alkanic. The viscosity of iso-alkanic waxes is greater than 10 mm2/s (at 100° C.) and the combined number average molecular weight is >600 g/mole.

Synthetic waxes are produced by means that are atypical for petroleum wax production and are thus not considered petroleum wax. The synthetic waxes may include waxes containing branched alkanes and copolymerized with monomers such as, but not limited to propylene, polyethylene, and Fischer Tropsch type waxes. Polyethylene wax is a synthetic wax containing alkane units of varying lengths having attached thereto ethylene monomers.

The natural waxes may include rice bran wax, bees' wax, carnauba wax or candelilla wax.

The waxes may be used alone or in any combination.

Function of Softeners

The selection of softeners has an influence on the softness of the base. Softeners modify the texture, cause the hydrophobic and hydrophilic components of the base to be miscible, and may further plasticize the synthetic elastomers of the gum base. The emulsifiers, which belongs to the group of softeners, provide the gum base with water-binding properties, which confer to the gum base a pleasant smooth surface and reduce its adhesive properties.

Softeners

Softeners suitable for use in the gum base include triglycerides of non-hydrogenated, partially hydrogenated and fully hydrogenated vegetable oils and tallow, cocoa butter and degreased cocoa powder and in addition to these the emulsifiers.

The group of triglycerides include cottonseed, palm, palm kernel, coconut, safflower, rapeseed, sunflower, tallow, soybean, cocoa butter, medium-chained triglycerides and the like.

The caproic, caprylic, capric, myristic, lauric and palmitic fatty acids of the triglycerides tend to plasticize the synthetic elastomers more than triglycerides containing predominantly stearic fatty acid To the group of emulsifiers belong the monoglycerides, diglycerides, acetylated mono and diglycerides, distilled mono- and diglycerides, glycerol monostearate, propylene glycol monostearate, Na-, K-, Mg- and Ca-stearates, glycerol triacetate, fatty acid monoglycerides (e.g. stearic, palmitic, oleic and linoleic acids), lactic acid esters and acetic acid esters of mono- and diglycerides, sugar esters of edible fatty acids also referred to as sucrose polyesters including those disclosed in WO 00/25598, lecithin and hydroxylated lecithin, most of these may contain triglyceride levels less than 2% by weight from their manufacturing processing, The softeners including the emulsifiers may be used alone or at least two or more in combination.

Function of Fillers

Fillers used in gum base modify the texture of the gum base and aid in processing. Particle size has an effect on cohesiveness, density and processing characteristics of the gum base and its compounding. The smaller the particle size, the more dense and cohesive the final gum base. Also, by selecting fillers based on their particle size distribution, initial mass compounding may be varied, thus allowing alteration of the compounding characteristics of the initial mass during gum base processing and ultimately the final chew characteristics of gums made from these gum bases.

Fillers

Fillers suitable for use in the gum base include magnesium and calcium carbonate, ground limestone and silicate types such as magnesium and aluminum silicate, kaolin and clay, aluminium oxide, silicium oxide, talc, as well as titanium oxide, mono-, di- and tricalcium phosphate, sodium sulphate, cellulose polymers such as ethyl, methyl and wood or mixtures thereof.

Talc filler may be used in the gum base and gum of the present invention that may come in contact with or employ acid flavours or provide an acidic environment needed to prevent degradation of an artificial sweetener by reacting with calcium carbonate type fillers. Mean particle size for calcium carbonate and talc fillers typically range from about 0.1 micron to about 15 microns.

The fillers may also include natural organic fibres such as fruit vegetable fibres, grain, rice, cellulose and combinations thereof.

Function and List of Other Optional Ingredients Such as Antioxidants, Colourants and Flavourants:

Antioxidants prolong shelf life and storage of gum base, finished gum or their respective components including fats and flavour oils.

Antioxidants suitable for use in gum base include butylated hydroxyanisole (BHA), butylated hydroxytoluene (BHT), betacarotenes, tocopherols, acidulants such as Vitamin C, propyl gallate, other synthetic and natural types or mixtures thereof.

Flavourants and colourants impart characteristics or remove or mask undesired characteristics. Colourants may typically include FD&C type lakes, plant extracts, fruit and vegetable extracts and titanium dioxide flavourants may typically include cocoa powder, heat-modified amino acids and other vegetable extracts.

Preparation of Gum Bases

Gum bases are typically prepared by adding an amount of the elastomer, elastomer plasticizer and filler, and on occasion a vinyl polymer, to a heated (10° C.-120° C.) sigma blade mixer with a front to rear speed ratio of from about 1.2:1 to about 2:1, the higher ratio typically being used for gum base which requires more rigorous compounding of its elastomers.

The initial amounts of ingredients comprising the initial mass may be determined by the working capacity of the mixing kettle in order to attain a proper consistency and by the degree of compounding desired to break down the elastomer and increase chain branching. The higher the level of filler at the start or selection of a filler having a certain particle size distribution, the higher the degree of compounding and thus more of the elastomeric chain crosslinking are broken, causing more branching of the elastomer thus lower viscosity gum bases and thus softer final gum base and gum made from such a gum base. The longer the time of compounding, the use of lower molecular weight or softening point gum base ingredients, the lower the viscosity and firmness of the final gum base.

Compounding typically begins to be effective once the ingredients have massed together. Anywhere from 15 minutes to 90 minutes may be the length of compounding time.

Preferably, the time of compounding is from 20 minutes to about 60 minutes. The amount of added elastomer plasticizer depends on the level of elastomer and filler present. If too much elastomer plasticizer is added, the initial mass becomes over plasticized and not homogeneous.

After the initial ingredients have massed homogeneously and compounded for the time desired, the balance of the gum base ingredients are added in a sequential manner until a completely homogeneous molten mass is attained. Typically, any remainder of elastomer, elastomer plasticizer, vinyl polymer and filler, are added within 60 minutes after the initial compounding time. The filler and the elastomer plasticizer would typically be individually weighed and added in portions during this time. The optional waxes and the softeners are typically added after the elastomer and elastomer plasticizers and during the next 60 minutes. Then the mass is allowed to become homogeneous before dumping.

Typical gum base processing times may vary from about one to about three hours, preferably from about 1½ to 2½ hours, depending on the formulation. The final mass temperature when dumped may be between 70° C. and 130° C. and preferably between 100° C. and 120° C. The completed molten mass is emptied from the mixing kettle into coated or lined pans, extruded or cast into any desirable shape and allowed to cool and solidify. Those skilled in the art will recognize that many variations of the above described procedure may be followed.

The Water-Soluble Portion of Chewing Gum.

The water-soluble portion of the chewing gum may comprise softeners, sweeteners, high intensity sweeteners, flavoring agents, acidulants, fillers, antioxidants, and other components that provide desired attributes. Softeners typically constitute from about 0.5% to about 25.0% by weight of the chewing gum. The bulking agents generally comprise from about 5% to about 90%, preferably from about 20% to about 80% of the chewing gum. High-intensity sweeteners in gum typically may range from about 0.01 to 0.50 weight percent. A flavoring agent may be present in the chewing gum in an amount within the range of from about 0.1 to about 30.0 weight percent of the gum.

Softeners

Softeners are added to the chewing gum in order to optimize the chewability and mouth feel of the gum.

Softeners contemplated for use in the gum include glycerin, modified lecithin and combinations thereof. Further aqueous sweetener solutions such as those containing sorbitol, hydrogenated starch hydrolysates, corn syrup and combinations thereof may be used as softeners.

Sweeteners

Bulk sweeteners include both sugar and sugarless components. Bulk sweeteners may typically constitute 5 to about 95% by weight of the chewing gum, more typically constitute 20 to about 80% by weight, and more commonly, 30 to 60% by weight of the gum.

The sweeteners often fill the role of bulking agents in the gum. The sweeteners are improving juiciness of the gum and are supporting the flavour profile of the gum. Sugar sweeteners generally include, but are not limited to, saccharide-containing components commonly known in the chewing gum art, such as sucrose, dextrose, maltose, saccharose, lactose, sorbose, dextrin, trehalose, D-tagatose, dried invert sugar, fructose, levulose, galactose, corn syrup solids, glucose syrup, hydrogenated glucose syrup, and the like, alone or in combination.

The sweetener can be used in combination with sugarless sweeteners.

Generally, sugarless sweeteners include components with sweetening characteristics but which are devoid of the commonly known sugars and comprise, but are not limited to, sugar alcohols such as sorbitol, mannitol, xylitol, hydrogenated starch hydrolyzates, maltitol, isomalt, erythritol, lactitol and the like, alone or in combination.

Depending on the particular sweetness release profile and shelf-life stability needed, bulk sweeteners can also be used in combination high-intensity sweeteners. Preferred high intensity sweeteners include, but are not limited to sucralose, aspartame, salts of acesulfame, alitame, saccharin and its salts, cyclamic acid and its salts, cyclamate, glycyrrhizin, dihydrochalcones, thaumatin, monellin, sterioside and the like, alone or in combination. In order to provide longer lasting sweetness and flavour perception, it may be desirable to encapsulate or otherwise control the release of at least a portion of the artificial sweetener. Such techniques as wet granulation, wax granulation, spray drying, spray chilling, fluid bed coating, coascervation, encapsulation in yeast cells and fibre extrusion may be used to achieve the desired release characteristics. The encapsulation can also be performed in another material such as resin.

Usage level of the artificial sweetener will vary greatly and will depend on such factors as potency of the sweetener, rate of release, desired sweetness of the product, level and type of flavour used and cost considerations. Thus, the active level of artificial sweetener may vary from 0.02 to about 8%. When carriers used for encapsulation are included, the usage level of the encapsulated sweetener will be proportionally higher.

Combinations of sugar and/or sugarless sweeteners may be used in chewing gum.

Additionally, the softener may also provide additional sweetness, if such softeners as aqueous sugar or alditol are used.

If a low calorie gum is desired, a low caloric bulking agent can be used. Examples of low caloric bulking agents include polydextrose; Raftilose, Raftilin; Fructooligosaccharides (NutraFlora@); Palatinose oligosaccharide; Guar Gum Hydrolysate (SunFiber@); or indigestible dextrin (Fibersol). However, other low calorie-bulking agents can be used.

Flavour

The chewing gum centres provided herein may contain aroma agents and flavouring agents including natural and synthetic flavourings e.g. in the form of natural vegetable components, essential oils, essences, extracts, powders, including acids and other substances capable of affecting the taste profile. Examples of liquid and powdered flavourings include coconut, coffee, chocolate, vanilla, grape fruit, orange, lime, menthol, liquorice, caramel aroma, honey aroma, peanut, walnut, cashew, hazelnut, almonds, pineapple, strawberry, raspberry, tropical fruits, cherries, cinnamon, peppermint, wintergreen, spearmint, eucalyptus, and mint, fruit essence such as from apple, pear, peach, strawberry, apricot, raspberry, cherry, pineapple, and plum essence. The essential oils include peppermint, spearmint, menthol, eucalyptus, clove oil, bay oil, anise, thyme, cedar leaf oil, nutmeg, and oils of the fruits (e.g. lemon, bergamot and orange) as mentioned above.

The chewing gum flavour may be a natural flavouring agent, which is freeze-dried, preferably in the form of a powder, slices or pieces of combinations thereof. The particle size may be less than 3 mm, preferably less than 2 mm, more preferably less than 1 mm, calculated as the longest dimension of the particle. The natural flavouring agent may be in a form where the particle size is from about 3 μm to 2 mm, such as from 4 μm to 1 mm. Preferred natural flavouring agents include seeds from a fruit e.g. from strawberry, blackberry and raspberry.

Various synthetic flavours, such as mixed fruit flavours may also be used in the present chewing gum centres. The aroma agent may be used in quantities smaller than those conventionally used. The aroma agents and/or flavours may be used in an amount of from 0.01 to about 30% by weight (preferably from 0.01 to about 15% by weight) of the final product depending on the desired intensity of the aroma and/or flavour used. Preferably, the content of aroma/flavour is in the range of from 0.2 to 3% by weight of the total composition.

Acidulants

Also various acids are used typically in combination with fruit flavours, such as adipinic acid, succinic acid, fumaric acid, citric acid, tartaric acid, malic acid, acetic acid, lactic acid, phosphoric acid and glutaric acid or salts thereof. They are typically added in amounts of 0.01 to 10%.

Fillers

Fillers suitable for use in the chewing gum include magnesium and calcium carbonate, ground limestone and silicate types such as magnesium and aluminum silicate, kaolin and clay, aluminium oxide, silicium oxide, talc, as well as titanium oxide, mono-, di- and tricalcium phosphate, sodium sulphate, cellulose polymers such as ethyl, methyl and wood or mixtures thereof.

Talc filler may be used in the chewing gum of the present invention that may come in contact with or employ acid flavours or provide an acidic environment needed to prevent degradation of an artificial sweetener by reacting with calcium carbonate type fillers. Mean particle size for calcium carbonate and talc fillers typically range from about 0.1 micron to about 15 microns.

The fillers may also include natural organic fibres such as fruit vegetable fibres, grain, rice, cellulose and combinations thereof.

Function and List of Other Ingredients Such as Antioxidants, Colourants and Taste Masking Agents:

Antioxidants prolong shelf life and storage of gum base, finished gum or their respective components including fats and flavour oils.

Antioxidants

Antioxidants suitable for use in gum base include butylated hydroxyanisole (BHA), butylated hydroxytoluene (BHT), betacarotenes, tocopherols, acidulants such as Vitamin C, propyl gallate, other synthetic and natural types or mixtures thereof.

Colourants

Colourants and whiteners may include FD & C-type dyes and lakes, fruit and vegetable extracts, titanium dioxide, and combinations thereof.

Taste Masking Agents

The taste masking agent improves the organoleptic properties of the product.

The masking agent include sucralose, zinc gluconate, ethyl maltol, glycine, acesulfame-K, aspartame, saccharin, fructose, xylitol, spray dried licorice root, glycerrhizine, dextrose, sodium gluconate, glucono delta-lactone, ethyl vanillin, vanillin, normal and high-potency sweeteners, and a variety of appropriate flavors.

Active Agents

The chewing gum according to the present invention may also comprise active agents other than nicotine. Active agents to be used in connection with the present invention may be any substance desired to be released from the chewing gum. If an accelerated rate of release is desired, corresponding to the effect obtained for the flavour, the primary substances are those with limited water solubility, typically below 10 g/100 ml including substances, which are entirely water insoluble. Examples are medicines, dietary supplements, oral compositions, anti-smoking agents, highly potent sweeteners, pH adjusting agents, etc.

Further examples of active ingredients include paracetamol, benzocaine, cinnarizine, menthol, carvone, coffeine, chlorhexidine-di-acetate, cyclizine hydrochloride, 1,8-cineol, nandrolone, miconazole, mystatine, aspartame, sodium fluoride, nicotine, saccharin, cetylpyridinium chloride, other quaternary ammonium compounds, vitamin E, vitamin A, vitamin D, glibenclamide or derivatives thereof, progesterone, acetylsalicylic acid, dimenhydrinate, cyclizine, metronidazole, sodium hydrogencarbonate, the active components from ginkgo, the active components from propolis, the active components from ginseng, methadone, oil of peppermint, salicylamide, hydrocortisone or astemizole.

Examples of active agents in the form of dietary supplements are for instance salts and compounds having the nutritive effect of vitamin B2 (riboflavin), B12, folinic acid, niacine, biotine, poorly soluble glycerophosphates, amino acids, the vitamins A, D, E and K, minerals in the form of salts, complexes and compounds containing calcium, phosphorus, magnesium, iron, zinc, copper, iodine, manganese, chromium, selenium, molybdenum, potassium, sodium or cobalt.

Furthermore, reference is made to lists of nutrients accepted by the authorities in different countries such as for instance US code of Federal Regulations, Title 21, Section 182.5013.182 5997 and 182.8013-182.8997.

Examples of active agents in the form of compounds for the care or treatment of the oral cavity and the teeth, are for instance bound hydrogen peroxide and compounds capable of releasing urea during chewing.

Examples of active agents in the form of antiseptics are for instance salts and compounds of guanidine and biguanidine (for instance chlorhexidine diacetate) and the following types of substances with limited water-solubility: quaternary ammonium compounds (for instance ceramine, chloroxylenol, crystal violet, chloramine), aldehydes (for instance paraformaldehyde), compounds of dequaline, polynoxyline, phenols (for instance thymol, para chlorophenol, cresol) hexachlorophene, salicylic anilide compounds, triclosan, halogenes (iodine, iodophores, chloroamine, dichlorocyanuric acid salts), alcools (3,4 dichlorobenzyl alcohol, benzyl alcohol, phenoxyethanol, phenylethanol), cf. furthermore Martindale, The Extra Pharmacopoeia, 28th edition, page 547-578; metal salts, complexes and compounds with limited water-solubility, such as aluminium salts, (for instance aluminium potassium sulfate AIK (S04) 2, 12H20) and furthermore salts, complexes and compounds of boron, barium, strontium, iron, calcium, zinc, (zinc acetate, zinc chloride, zinc gluconate), copper (copper chloride, copper sulfate), lead, silver, magnesium, sodium, potassium, lithium, molybdenum, vanadium should be included; other compositions for the care of mouth and teeth: for instance; salts, complexes and compounds containing fluorine (such as sodium fluoride, sodiummonofluorophosphate, aminofluorides, stannous fluoride), phosphates, carbonates and selenium.

Cf. furthermore J. Dent. Res. Vol. 28 No. 2, page 160-171, 1949, wherein a wide range of tested compounds are mentioned.

Examples of active agents in the form of agents adjusting the pH in the oral cavity include for instance: acceptable acids, such as adipinic acid, succinic acid, fumaric acid, or salts thereof or salts of citric acid, tartaric acid, malic acid, acetic acid, lactic acid, phosphoric acid and glutaric acid and acceptable bases, such as carbonates, hydrogen carbonates, phosphates, sulfates or oxides of sodium, potassium, ammonium, magnesium or calcium, especially magnesium and calcium.

Examples of active agents in the form of anti-smoking agents include for instance: nicotine, tobacco powder or silver salts, for instance silver acetate, silver carbonate and silver nitrate.

Further examples of active agents are medicines of any type.

Examples of active agents in the form of medicines include coffeine, salicylic acid, salicyl amide and related substances (acetylsalicylic acid, choline salicylate, magnesium salicylate, sodium salicylate), paracetamol, salts of pentazocine (pentazocine hydrochloride and pentazocinelactate), buprenorphine hydrochloride, codeine hydrochloride and codeine phosphate, morphine and morphine salts (hydrochloride, sulfate, tartrate), methadone hydrochloride, ketobemidone and salts of ketobemidone (hydrochloride), beta-blockers, (propranolol), calcium antagonists, verapamil hydrochloride, nifedinpine as well as suitable substances and salts thereof mentioned in Pharm. Int., Nov. 85, pages 267-271, Barney H. Hunter and Robert L. Talbert, nitroglycerine, erythrityl tetranitrate, strychnine and salts thereof, lidocaine, tetracaine hydrochloride, etorphine hydrochloride, atropine, insulin, enzymes (for instance papain, trypsin, amyloglucosidase. glucoseoxidase, streptokinase, streptodornase, dextranase, alpha amylase), polypeptides (oxytocin, gonadorelin, (LH. RH), desmopressin acetate (DDAVP), isoxsuprine hydrochloride, ergotamine compounds, chloroquine (phosphate, sulfate), isosorbide, demoxytocin, heparin.

Other active ingredients include beta-lupeol, Letigen, Sildenafil citrate and derivatives thereof.

Dental products include Carbami, CPP Caseine Phospho Peptide; Chlorhexidine, Chlorhexidine di acetate, Chlorhexidine Chloride, Chlorhexidine di gluconate, Hexetedine, Strontium chloride, Potassium Chloride, Sodium bicarbonate, Sodium carbonate, Fluor containing ingredients, Fluorides, Sodium fluoride, Aluminium fluoride, Ammonium fluoride, Calcium fluoride, Stannous fluoride, Other fluor containing ingredients Ammonium fluorosilicate, Potassium fluorosilicate, Sodium fluorosilicate, Ammonium monofluorphosphate, Calcium monofluorphosphate, Potassium monofluorphosphate, Sodium monofluorphosphate, Octadecentyl Ammonium fluoride, Stearyl Trihydroxyethyl Propylenediamine Dihydrofluoride, Vitamins include A, B1, B2, B6, B12, Folin acid, niacin, Pantothensyre, biotine, C, D, E, K.

Minerals include Calcium, phosphor, magnesium, iron, Zink, Cupper, Iod, Mangan, Crom, Selene, Molybden. Other active ingredients include: Q10@, enzymes. Natural drugs including Ginkgo Biloba, ginger, and fish oil. The invention also relates to use of migraine drugs such as Serotonin antagonists: Sumatriptan, Zolmitriptan, Naratriptan, Rizatriptan, Eletriptan; nausea drugs such as Cyclizin, Cinnarizin, Dimenhydramin, Difenhydrinat; hay fever drugs such as Cetrizin, Loratidin, pain relief drugs such as Buprenorfin, Tramadol, oral disease drugs such as Miconazol, Amphotericin B, Triamcinolonaceton; and the drugs Cisaprid, Domperidon, Metoclopramid.

Preparation of Chewing Gum

In general, chewing gum may be manufactured by sequentially adding the various chewing gum ingredients to a commercially available mixer known in the art. After the initial ingredients have been thoroughly mixed, the gum mass is discharged from the mixer and shaped into the desired form such as by rolling into sheets and cutting into sticks, extruded into chunks or casting into pellets.

Generally, the ingredients may be mixed by first melting the gum base and adding it to the running mixer. Colors, active agents and/or emulsifiers may also be added at this time. A softener such as glycerin may also be added at this time, along with syrup and a portion of the bulking agent/sweetener. Further portions of the bulking agent/sweetener may then be added to the mixer. A flavoring agent is typically added with the final portion of the bulking agent/sweetener. A high-intensity sweetener is preferably added after the final portion of bulking agent and flavor have been added.

The entire mixing procedure typically takes from five to fifteen minutes, but longer mixing times may sometimes be required. Those skilled in the art will recognize that many variations of the above described procedure may be followed. Including the one-step method described in US patent application 2004/0115305 hereby incorporated as reference.

Structure of the Chewing Gum

According to the invention, the form and shape of the nicotine chewing gum may be any suitable and user friendly structure. Accordingly, the gum centre or gum may be e.g. in a form selected from a pellet, a cushion-shaped pellet, a stick, a tablet, a chunk, a pastille, a pill, a ball and a sphere. Chewing gums are formed by extrusion, compression, rolling and may be centre filled with liquids and/or solids in any form.

Coating

In accordance with the invention, the chewing gum element may comprise about 0.1 to about 75% by weight of an outer coating applied onto the chewing gum centre. Thus, suitable coating types include hard coatings, film coatings and soft coatings of any composition including those currently used in coating of chewing gum, pharmaceutical products and confectioneries and any combination thereof.

One presently preferred outer coating type is a hard coating, which term is used in the conventional meaning of that term including sugar coatings and sugar-free (or sugarless) coatings and combinations thereof. The object of hard coating is to obtain a sweet, crunchy layer, which is appreciated by the consumer and it may moreover protect the gum centres for various reasons. In a typical process of providing the chewing gum centres with a protective sugar coating, the gum centres are successively treated in suitable coating equipment with aqueous solutions of crystallisable sugar such as sucrose or dextrose, which, depending on the stage of coating reached, may contain other functional ingredients, e.g. fillers, binding agents, colours, etc. In the present context, the sugar coating may contain further functional or active compounds including flavour compounds and/or pharmaceutically active compounds.

In the production of chewing gum it may, however, be preferred to replace the cariogenic sugar compounds in the coating by other, preferably crystallisable, sweetening compounds that do not have a cariogenic effect. In the art such coating are generally referred to as sugarless or sugar-free coatings. Presently preferred non-cariogenic hard coating substances include polyols, e.g. sorbitol, maltitol, mannitol, xylitol, erythritol, lactitol, isomalt and tagatose which are obtained by industrial methods by hydrogenation of D-glucose, maltose, fructose or levulose, xylose, erythrose, lactose, isomaltulose and D-galactose, respectively and trehalose, which is a non-cariogene mono-di-saccharide.

In a typical hard coating process as it will be described in details in the following, a suspension containing crystallisable sugar and/or polyol is applied onto the gum centres and the water it contains is evaporated off by blowing with air. This cycle must be repeated several times, typically 3 to 80 times, in order to reach the swelling required. The term "swelling" refers to the increase in weight or thickness of the products, as considered at the end of the coating operation by comparison with the beginning, and in relation to the final weight or thickness of the coated products. In accordance with the present invention, the coating layer constitutes about 0.1 to about 75% by weight of the finished chewing gum element, such as about 10 to about 60% by weight, including about 15 to about 50% by weight.

In further useful embodiments the outer coating of the chewing gum element of the invention is an element that is subjected to a film coating process and which therefore comprises one or more film-forming polymeric agents and optionally one or more auxiliary compounds, e.g. plasticizers, pigments and opacifiers. A film coating is a thin polymer-based coating applied to a chewing gum centre of any of the above forms. The thickness of such a coating is usually between 20 and 100 μm.

Generally, the film coating is obtained by passing the chewing gum centres through a spray zone with atomised droplets of the coating materials in a suitable aqueous or organic solvent vehicle, after which the material adhering to the gum centres is dried before the next portion of coating is received. This cycle is repeated until the coating is complete.

In the present context, suitable film-coating polymers include edible cellulose derivatives such as cellulose ethers including methylcellulose (MC), hydroxyethyl cellulose (HEC), hydroxypropyl cellulose (HPC) and hydroxypropyl methylcellulose (HPMC). Other useful film-coating agents are acrylic polymers and copolymers, e.g. methylacrylate aminoester copolymer or mixtures of cellulose derivatives and acrylic polymers. A particular group of film-coating polymers, also referred to as functional polymers are polymers that, in addition to its film-forming characteristics, confer a modified release performance with respect to active components of the chewing gum formulation. Such release modifying polymers include methylacrylate ester copolymers, ethylcellulose (EC) and enteric polymers designed to resist the acidic stomach environment, yet dissolve readily in the duodenum. The latter group of polymers include: cellulose acetate phtalate (CAP), polyvinyl acetate phtalate (PVAP), shellac, metacrylic acid copolymers, cellulose acetate trimellitate (CAT) and HPMC. It will be appreciated that the outer film coating according to the present invention may comprise any combination of the above film-coating polymers.

In other embodiments, the film coating layer of the chewing gum elements according to the invention comprises a plasticizing agent having the capacity to alter the physical properties of a polymer to render it more useful in performing its function as a film-forming material. In general, the effect of plasticizers will be to make the polymer softer and more pliable as the plasticizer molecules interpose themselves between the individual polymer strands thus breaking down polymer-polymer interactions. Most plasticizers used in film coating are either amorphous or have very little crystallinity. In the present context, suitable plasticizers include polyols such as glycerol, propylene glycol, polyethylene glycol, e.g. the 200-6000 grades hereof, organic esters such as phtalate esters, dibutyl sebacate, citrate esters and thiacetin, oils/glycerides including castor oil, acetylated monoglycerides and fractionated coconut oil.

The choice of film-forming polymer(s) and plasticizing agent(s) for the outer coating of the present chewing gum element is made with due consideration for achieving the best possible barrier properties of the coating in respect of dissolution and diffusion across the film of moisture and gasses.

The film coating of the chewing gum elements may also contain one or more colourants or opacifiers. In addition to providing a desired colour hue, such agents may reflect light or form a barrier against moisture and gasses. Suitable colourants/pacifiers include organic dyes and their lakes, inorganic colouring agents, e.g. titanium oxide and natural colours such as e.g. .beta.-carotene or chlorophyll.

Additionally, film coatings may contain one or several auxiliary substances such as flavours and waxes or saccharide compounds such as polydextrose, dextrins including maltodextrin, lactose, modified starch, a protein such as gelatine or zein, a vegetable gum and any combination thereof.

In one specific embodiment the chewing gum centre is in the form of a stick which is provided on at least one side with an edible film comprising layer of a coating of a film forming agent, e.g. a cellulose derivative, a modified starch, shallac, gum arabic, a dextrin, gelatine, zein, a vegetable gum, a synthetic polymer and any combination thereof, and a wax such as beeswax, carnauba wax, microcrystalline wax, paraffin wax and combinations thereof.

The following examples are given for illustration, but not limitation of the invention.

TABLE 1

| Ingredient | Example 2 Product I1 | Example 3 Product I2 | Example 4 Product I3 |
| --- | --- | --- | --- |
| Elastomers | 6 | 12 | 3 |
| Elastomer plasticizers | 30 | 20 | 15 |
| Waxes | 8 | 8 | 4 |
| Softeners | 6 | 6 | 3 |
| Antioxidant | 0.1 | 0.1 | 0.1 |
| Calciumcarbonate | 20 | 25 | 15 |
| Bulk sweetener | 21 | 20 | 51 |

TABLE 1-continued

| Ingredient | Example 2 Product I1 | Example 3 Product I2 | Example 4 Product I3 |
|---|---|---|---|
| Nicotine compound | 1.4 | 1.4 | 1.4 |
| Buffer | 3.0 | 3.0 | 3.0 |
| High Intensity Sweetener | 0.3 | 0.3 | 0.3 |
| Flavours | 3.2 | 3.2 | 3.2 |
| Glycerine | 1 | 1 | 1 |
| Total | 100.0 | 100.0 | 100.0 |

Example 1

Preparation of Gum Base

Gum bases are prepared, which comprises the following ingredients:
Elastomers
Elastomer plasticizers
Waxes
Softeners
Fillers
Anti oxidants The detailed formulations are given in table 1. It should be emphasized that several other gum base compositions may be applied within the scope of the invention.

The elastomers and fillers are added to the mixing kettle provided with mixing means like e.g. horizontally placed Z-shaped arms. The kettle had been preheated for 15 minutes to a temperature of about 120° C. The rubber is broken into small pieces and softened with mechanical action in the kettle.

The elastomer plasticizer is slowly added to the elastomer until the mixture becomes homogeneous. The remaining elastomer plasticizer is then added to the kettle and mixed for 10-20 minutes. The softening ingredients are added and mixed for 20-40 minutes until the whole mixture becomes homogeneous.

The mixture is then discharged into a pan and allowed to cool to room temperature from the discharge temperature of 120° C.

Example 2

Chewing gum is prepared by use of the gum base in example 1 formulated according to table 1. A conventional mechanical mixing procedure is used with the use of only moderate heating.

Gum base and filler is mixed in a mixing kettle provided with mixing means like e.g. horizontally placed Z-shaped arms. The kettle had been preheated to a temperature of up to approximately 50° C.

When the content is homogeneous the other ingredients are added according to a specified time schedule. Nicotine is added in the first half of the mixing process.

The pieces may be formulated with 0.1-8 mg of nicotine per piece preferably 2-4 mg. The pieces evaluated comprise 2 mg nicotine per piece.

The chewing gum was coated by means of hard coating. The coating may e.g. be applied according to the methods disclosed in the U.S. Pat. No. 6,627,234, hereby included by reference.

Example 3

Chewing gum is prepared by use of the gum base in example 1 formulated according to table 1. A conventional mechanical mixing procedure is used with the use of only moderate heating.

Gum base and filler is mixed in a mixing kettle provided with mixing means like e.g. horizontally placed Z-shaped arms. The kettle had been preheated to a temperature of up to approximately 50° C.

When the content is homogeneous the other ingredients are added according to a specified time schedule. Nicotine is added in the first half of the mixing process.

The pieces may be formulated with 0.1-8 mg of nicotine per piece preferably 2-4 mg. The pieces evaluated comprise 2 mg nicotine per piece.

The chewing gum was coated by means of hard coating. The coating may e.g. be applied according to the methods disclosed in the U.S. Pat. No. 6,627,234, hereby included by reference.

Example 4

Chewing gum is prepared by use of the gum base in example 1 formulated according to table 1. A conventional mechanical mixing procedure is used with the use of only moderate heating.

Gum base and filler are mixed in a mixing kettle provided with mixing means like e.g. horizontally placed Z-shaped arms. The kettle had been preheated to a temperature of up to approximately 50° C.

When the content is homogeneous the other ingredients are added according to a specified time schedule. Nicotine is added in the first half of the mixing process.

The pieces may be formulated with 0.1-8 mg of nicotine per piece preferably 2-4 mg. The pieces evaluated comprise 2 mg nicotine per piece.

The chewing gum was coated by means of hard coating. The coating may e.g. be applied according to the methods disclosed in the U.S. Pat. No. 6,627,234, hereby included by reference.

Example 5

The release of the active agent in Example 2-4 and two commercial products are determined in vitro. The test in vitro is carried out on a chewing machine (European Pharmacopeia 4 th. ed. 2.9.25 Chewing gum medicated, drug release from) by chewing one piece of chewing gum at specified time intervals 0, 1, 2, 3, 5, 7.5, 10, 20 and 30 minutes in a phosphate buffer with a pH of 7.4.

The results are illustrated and explained below

FIG. 1 illustrates a release profile of two prior art nicotine chewing gums as a function of time.

It is noted that the very initial and the intermediate release, is relatively low over the period corresponding to a typical smoking time i.e. 5-8 minutes. The release rate from 0-1 minutes is even lower than the remaining intermediate release.

The two prior art nicotine chewing gums PA1 and PA2 are both intended for use by means of a chew process over approximately thirty minutes. In other words, the intended build-up of nicotine in the blood of the user is a process running over quite a long while.

It is noted that both nicotine chewing gums appear to be releasing relatively linear.

Figure 2:
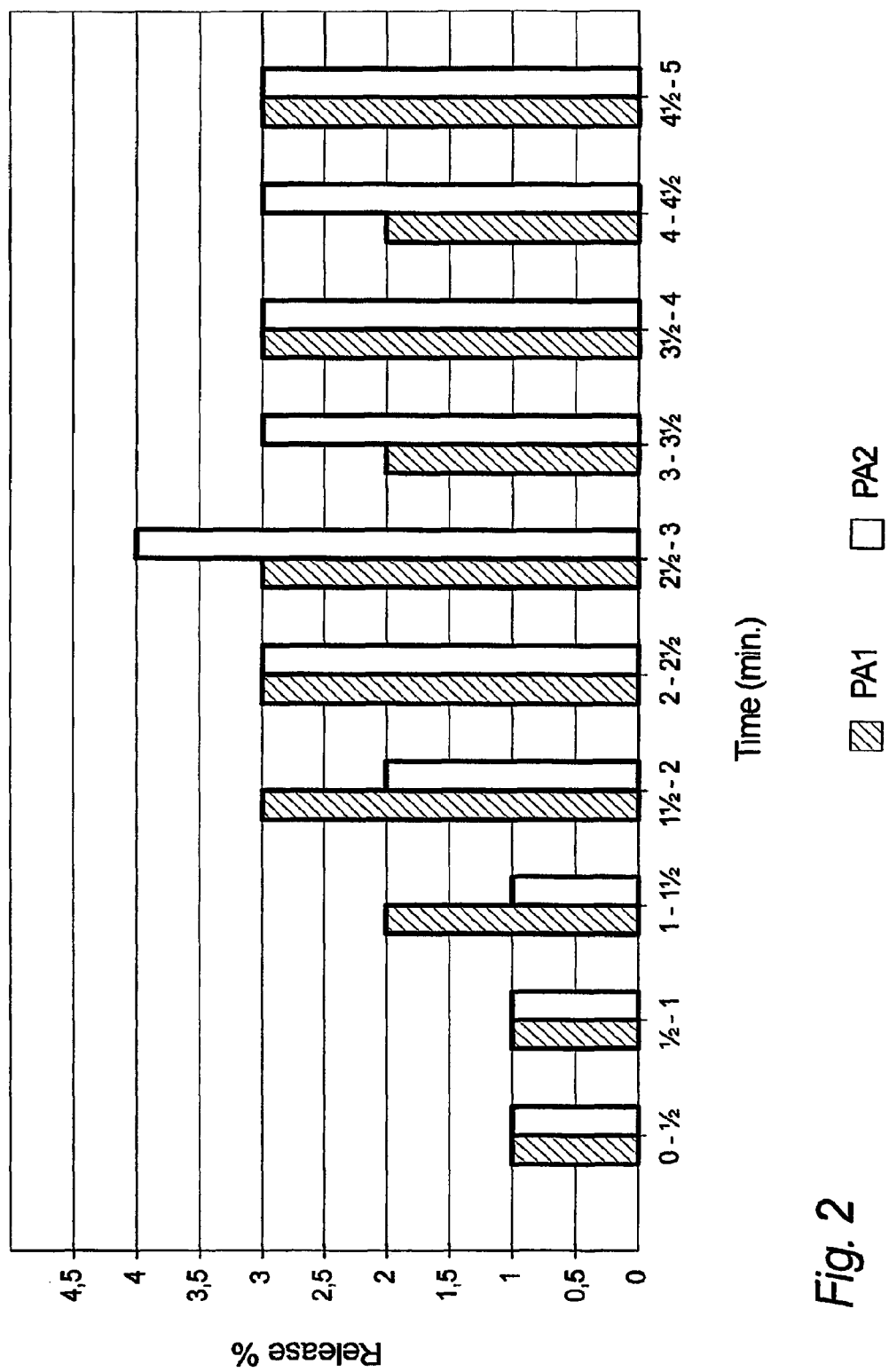
FIG. 2 shows a break-up of the release in 30-second intervals of the intermediate release of prior art nicotine chewing gums.

FIG. 2 illustrates the release of FIG. 1 in specific intervals of the above-mentioned chewing gums PA1 and PA2 over the initial chewing period of 0 to 5 minutes in intervals of 30 seconds. In other words a sort of differential illustration of the release focusing on the release in the individual sub-periods of the illustrated release time. As illustrated, the evaluated sub-periods are 0-½ minute, ½-1 minute, 1 minute-1½ minute, 1½ minute-2 minute, 2 minute-2½ minute, 2½ minute-3 minute, 3 minute-3½ minute, 3½-4 minutes, 4-4½ minutes and 4½-5 minutes.

It is noted that the very initial release and intermediate release, is increasing relatively slow over a relatively long period compared to a typical smoking time in spite of the fact that the release showed in FIG. 1 appeared to be relatively constant.

Figure 3:
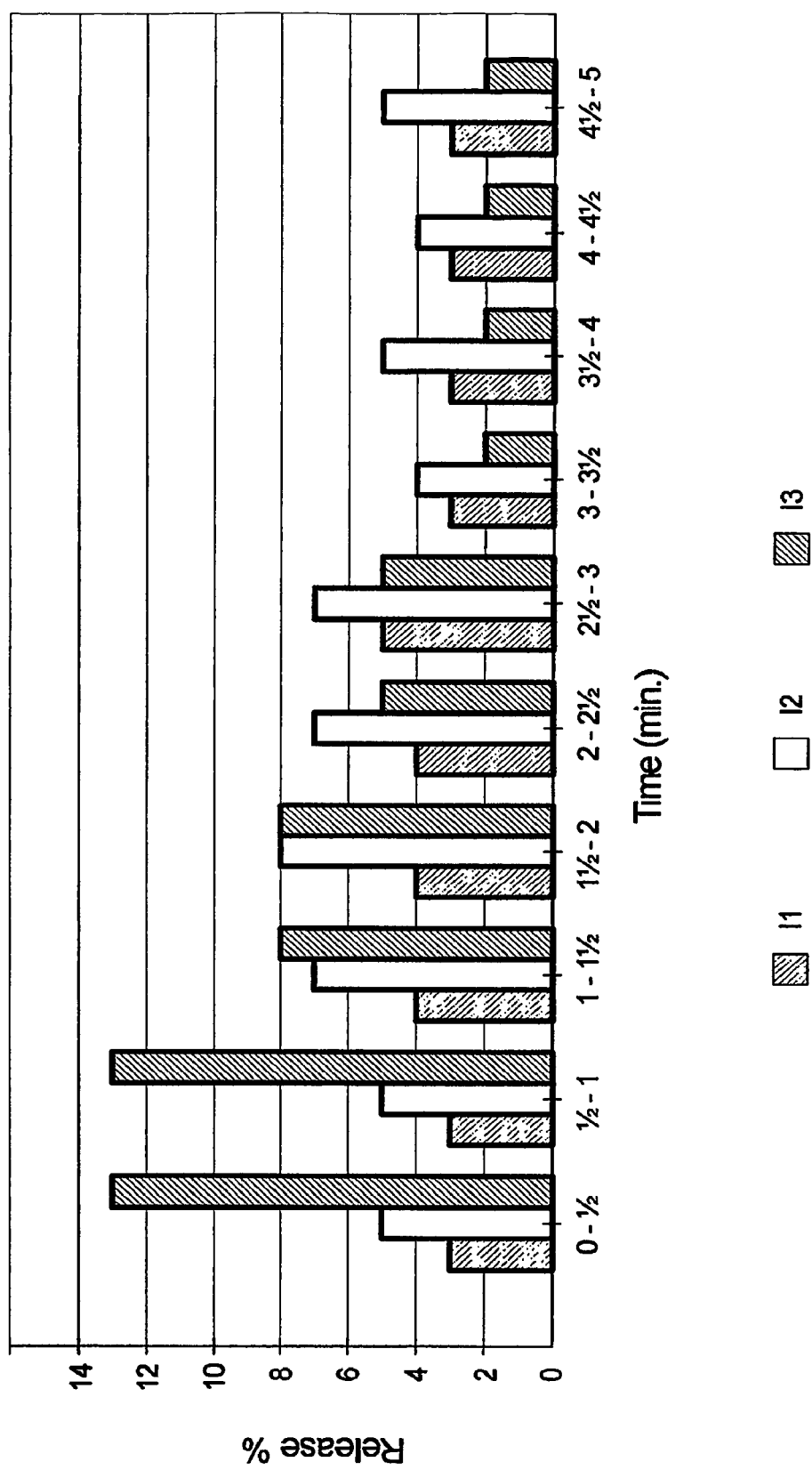
FIG. 3 shows a break-up of the release in 30 second intervals of the intermediate release of nicotine chewing gums applied according to the invention.

FIG. 3 illustrates the initial and intermediate release of three chewing gums I1, I2 and I3 applicable according to the invention. The release, or transfer from the chewing gum to the exterior of the chewing gum, is illustrated in the same way as the prior art chewing gums of FIG. 2.

The illustrated chewing gums benefit of an initial advantageous release over the complete critical period of the first five to eight minutes of smoking. It is thus noted that the release is never below 2% per sub period, i.e. 30 seconds. In other words, when the chewing gum is applied according to the invention, a constant amount of nicotine may be available for transfer into the blood via the mucosa membrane.

It is also noted that the chewing 13 features a very significant release in the first few minutes of the chewing process, thereby facilitating a fast relief due to the fact that a high osmotic pressure on the mucosa membrane may be maintained from the very beginning.

It is further noted that the chewing gum I1 and I2 features a very constant release over the first 5 minutes of chewing. This may be regarded very advantageous when complying with e.g. the taste problem related to nicotine in the mouth.

FIG. 3 illustrates the resulting release obtained when a nicotine chewing gum is chewed in a chewing machine.

According to the invention, a nicotine chewing gum having the properties as illustrated in FIG. 3 may be applied according to the following process steps.

A nicotine chewing gum, e.g. I1, I2 or I3 is provided to a user having a human body. The human user may then chew the chosen nicotine chewing gum and a fast relief with respect to craving may be obtained by the transfer of nicotine from the nicotine chewing gum to the blood of the user via the mucosa membrane.

As the applied nicotine chewing gum features a transfer of nicotine from the chewing gum above a chosen threshold transfer rate in the period of about ½ minute to about 2½ minutes from initiation of said chewing process a constant osmotic pressure may be maintained on the mucosa membrane during a relatively long intermediate period of the chewing process. In this way, a fast relief has been according to an embodiment of the invention.

It is noted that none of the chewing gums applied according to the invention features a transfers of nicotine from the chewing gum below 2 mg of nicotine per 30 second. It is also noted that e.g. I2 features a maintained dose of never below 4 mg per 30 second.

Figure 4:
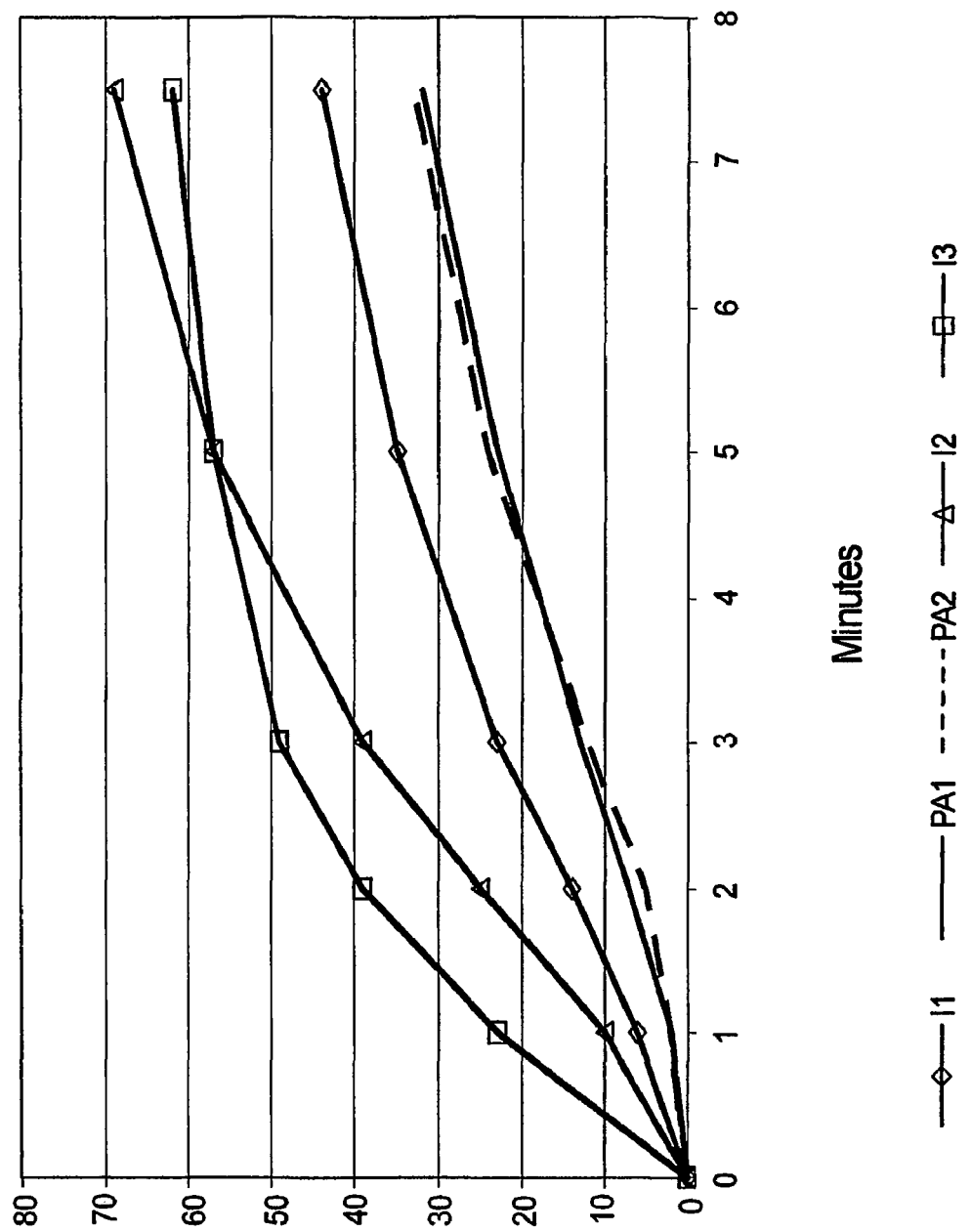
FIG. 4 shows a release profile of a combination of prior art chewing gums and chewing gums according to the invention.

FIG. 4 illustrates the initial and intermediate release from the above discussed chewing gums PA1, PA2, I1, I2 and I3 over the initial approximately 8 minutes of the chewing process. It is noted that the quickest releaser tends to flatten out after about 4-5 minutes of chewing.

What is claimed is:

1. Chewing gum for release of tobacco alkaloid, wherein said chewing gum comprises flavour in an amount of about 0.001 to about 30% by weight and sweeteners in an amount of about 2% to about 80% by weight, wherein said chewing gum comprises elastomers in an amount of about 0.1 to about 12% by weight of the chewing gum, wherein said chewing gum comprises elastomer plasticizers in an amount of about 2 to about 30% by weight of the chewing gum, and wherein at least 0.03 mg of the tobacco alkaloid comprised in said chewing gum prior to chewing will be in vitro released within every 30 seconds in the period from ½ minutes to about 2½ minutes from initiation of a chewing process on a chewing machine in accordance with European Pharmacopeia 4th. ed. 2.9.25, with a phosphate buffer with a pH of 7.4.

2. Chewing gum according to claim 1, wherein said tobacco alkaloid comprises nicotine.

3. Chewing gum according to claim 1, wherein at least 2% of the tobacco alkaloid comprised in said chewing gum prior to chewing will be in vitro released within every 30 seconds in the period from ½ minutes to about 2½ minutes from initiation of said chewing process.

4. Chewing gum according to claim 1, wherein at least 3% of the tobacco alkaloid comprised in said chewing gum prior to chewing will be in vitro released within every 30 seconds in the period from about ½ minute to about 2½ minutes from initiation of said chewing process.

5. Chewing gum according to claim 1, wherein at least 5% of the tobacco alkaloid comprised in said chewing gum prior to chewing will be in vitro released within every 30 seconds in the period from about ½ minute to about 2½ minutes from initiation of said chewing process.

6. Chewing gum according to claim 1, wherein at least 2% of the tobacco alkaloid comprised in said chewing gum prior to chewing will be in vitro released within every 30 seconds in the period of about 2½ minutes to about 5 minutes from initiation of said chewing process.

7. Chewing gum according to claim 1, wherein at least 3% of the tobacco alkaloid comprised in said chewing gum prior to chewing will be in vitro released within every 30 seconds in the period of about 2½ minutes to about 5 minutes from initiation of said chewing process.

8. Chewing gum according to claim 1, wherein at least 4% of the tobacco alkaloid comprised in said chewing gum prior to chewing will be in vitro released within every 30 seconds in the period of about 5 minutes to about 10 minutes from initiation of said chewing process.

9. Chewing gum according to claim 1, wherein at least 2 to 10% of the tobacco alkaloid comprised in said chewing gum prior to chewing will be in vitro released within the period of about 0 seconds to about 30 seconds from initiation of said chewing process.

10. Chewing gum according to claim 1, wherein less than 14% of the tobacco alkaloid comprised in said chewing gum prior to chewing will be in vitro released within the period of about 0 seconds to about 2½ minutes from initiation of said chewing process.

11. Chewing gum according to claim 1, wherein at most 18% of the tobacco alkaloid comprised in said chewing gum prior to chewing will be in vitro released within the period of about 10 to about 30 minutes from initiation of said chewing process.

12. Chewing gum according to claim 1, wherein at least 0.05 mg of the tobacco alkaloid comprised in said chewing gum prior to chewing will be in vitro released within every 30

13. Chewing gum according to claim 1, wherein at least 0.08 mg of the tobacco alkaloid comprised in said chewing gum prior to chewing will be in vitro released within every 30 seconds in the period from about ½ minute to about 2½ minutes from initiation of said chewing process.

14. Chewing gum according to claim 1, wherein at least 0.03 mg of the tobacco alkaloid comprised in said chewing gum prior to chewing will be in vitro released within every 30 seconds in the period of about 2½ to about 5 minutes from initiation of said chewing process.

15. Chewing gum according to claim 1, wherein at least 0.05 mg of the tobacco alkaloid comprised in said chewing gum prior to chewing will be in vitro released within every 30 seconds in the period of about 2½ minutes to about 5 minutes from initiation of said chewing process.

16. Chewing gum according to claim 1, wherein at least 0.08 mg of the tobacco alkaloid comprised in said chewing gum prior to chewing will be in vitro released within every 30 seconds in the period of about 2½ minutes to about 5 minutes from initiation of said chewing process.

17. Chewing gum according to claim 1, wherein at least 0.5 mg of tobacco alkaloid is released within the initial 10 minutes of the chewing process.

18. Chewing gum according to claim 1, wherein different parts of the chewing gum are targeted for tobacco alkaloid transfer at different times or in different periods of the chewing process.

19. Chewing gum according to claim 1, wherein said chewing gum comprises a coating and wherein said coating comprises tobacco alkaloid.

20. Chewing gum according to claim 1, wherein said chewing gum comprises hydrophilic polymers.

21. Chewing gum according to claim 1, wherein said tobacco alkaloid is comprised in an ion exchange resin.

22. Chewing gum according to claim 1, wherein said tobacco alkaloid comprises salts of nicotine.

23. Chewing gum according to claim 1, wherein said tobacco alkaloid comprises nicotine in its free from.

24. Chewing gum according to claim 1, wherein the tobacco alkaloid is buffered.

25. Chewing gum according to claim 1, wherein the chewing process is less than 30 minutes.

26. Chewing gum according to claim 1, wherein said chewing gum comprises fillers in an amount of from about 0 to about 60% by weight, flavour in an amount of about 0.001 to about 30% by weight and sweeteners in an amount of about 2 to about 80% by weight.

27. Chewing gum according to claim 1, wherein said chewing gum comprises high intensity sweeteners in an amount of from about 0.001 to about 3% by weight and flavour in an amount of about 0.001 to about 30% by weight.

28. Chewing gum according to claim 1, wherein the chewing gum comprises elastomers in an amount of about 2 to about 12% by weight of the chewing gum.

29. Chewing gum according to claim 1, wherein the chewing gum comprises elastomer plasticizers in an amount of about 5 to about 30% by weight of the chewing gum.

30. Chewing gum according to claim 1, wherein the chewing gum further comprises wax in an amount of about 0 to about 30% by weight of the chewing gum.

31. Chewing gum according to claim 1, wherein the chewing gum further comprises softeners in an amount of about 2 to about 30% by weight of the chewing gum.

32. Chewing gum according to claim 1, wherein the chewing gum further comprises fillers in an amount of about 0 to about 50% by weight of the chewing gum.

33. Chewing gum according to claim 1, wherein the chewing gum further comprises antioxidants in an amount of about 0 to about 5% by weight of the chewing gum.

34. Chewing gum according to claim 1, wherein said chewing gum is a compressed chewing gum.

35. Chewing gum according to claim 1, wherein said chewing gum comprises 2-4 mg of nicotine.

36. Chewing gum according to claim 1, wherein said chewing gum comprises 2 mg of nicotine.

37. Chewing gum according to claim 1, wherein said chewing gum comprises 0.1 to 75% by weight of an outer coating.

38. Chewing gum according to claim 1, wherein said tobacco alkaloid is comprised in tobacco powder.

* * * * *